Figure 1:
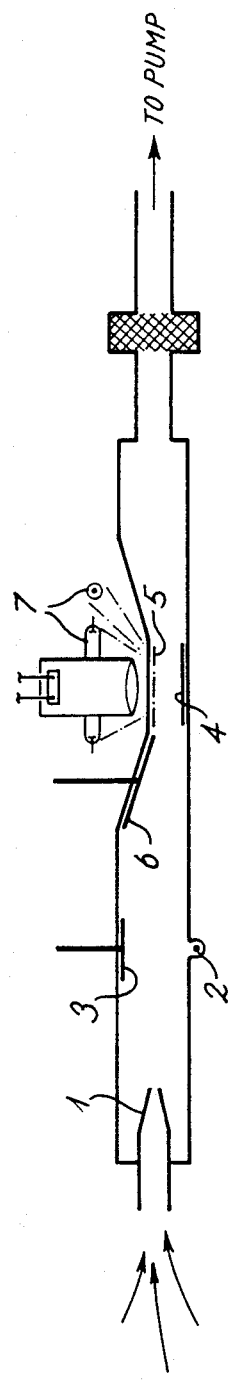
Figure 1:
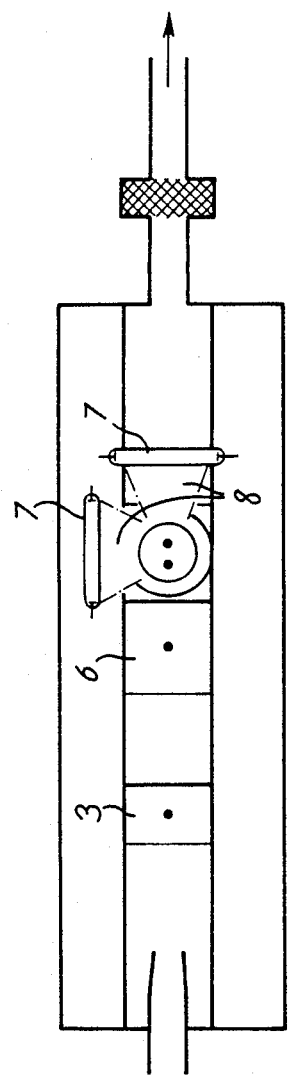

United States Patent [19]

Rood et al.

[11] Patent Number: 4,916,325
[45] Date of Patent: Apr. 10, 1990

[54] METHOD AND APPARATUS FOR THE MEASUREMENT OF AIRBORNE FIBRES BY THE ILLUMINATION OF FIBROUS PARTICLES PRECIPITATED ON A SURFACE

[75] Inventors: Anthony P. Rood; Edward J. Walker, both of London, England

[73] Assignee: National Research Development Corporation, London, England

[21] Appl. No.: 250,256

[22] Filed: Sep. 27, 1988

[30] Foreign Application Priority Data

Sep. 30, 1987 [GB] United Kingdom ................. 8722982

[51] Int. Cl.$^4$ ............................................ G01N 15/06
[52] U.S. Cl. .................................................. 250/573
[58] Field of Search ............... 250/564, 573, 574, 575, 250/576; 356/244, 245, 337, 338, 339, 340, 341, 342, 343, 442

[56] References Cited

U.S. PATENT DOCUMENTS 4,166,703 9/1979 Kirsch et al. ....................... 250/573

Primary Examiner—David C. Nelms
Attorney, Agent, or Firm—Cushman, Darby & Cushman

[57] ABSTRACT

Apparatus for measuring the quantity of fibres present in a gaseous fluid is based on the use of a nozzle to align the orientation of fibrous particles as they flow into a chamber. A charge is applied to the particles which are then precipitated on to a carrier. They are sequentially illuminated in directions normal and transverse to the direction of orientation and from measurements of the relative attenuation of the radiation, an indication of the number of precipitated particles is derived.

9 Claims, 2 Drawing Sheets

METHOD AND APPARATUS FOR THE MEASUREMENT OF AIRBORNE FIBRES BY THE ILLUMINATION OF FIBROUS PARTICLES PRECIPITATED ON A SURFACE

This invention relates to the measurement of airborne fibres and, in particular to apparatus suitable for the measurement of the level of asbestos fibres in the air.

Some fibrous dusts present a hazard to man when inhaled as they have been shown to be human carcinogens. Asbestos fibres are the best known example, and are controlled in the workplace by filtering a known volume of air, and examining the sample under phase contrast optical microscopy. By counting fibres, a concentration in the original air can be determined.

There is a need for a cheap portable instrument that directly indicates the levels of fibres without the need to wait for a filter sample and microscope examination. Leak testing during the stripping of fibrous insulation is an example. To that end a new approach to fibrous aerosol monitoring has been made by combining the electrostatic precipitation of aligned fibres with differential light scattering along and at right angles to the fibre axis.

A prototype instrument has been constructed based on a parallel-plate precipitator with inertial fibre alignment. Fibre detection is based on a difference circuit which measures the scattered light from two low powered flash-lamps. The instrument is calibrated to read in fibres per ml of air sampled.

According to the present invention there is provided apparatus for measuring the quantity of fibres present in a gaseous fluid comprising means for creating a flow of said gaseous fluid through a chamber, aligning means to align the orientation of fibrous particles flowing into said chamber, electrical charging means to charge said particles within said chamber, electrical precipitating means to precipitate said fibrous particles on to carrier means, illuminating means to illuminate said carrier means with radiation and measuring means to measure radiation transmitted from said carrier means, thereby to derive an indication of the number of said particles precipitated thereon.

Figure 2:
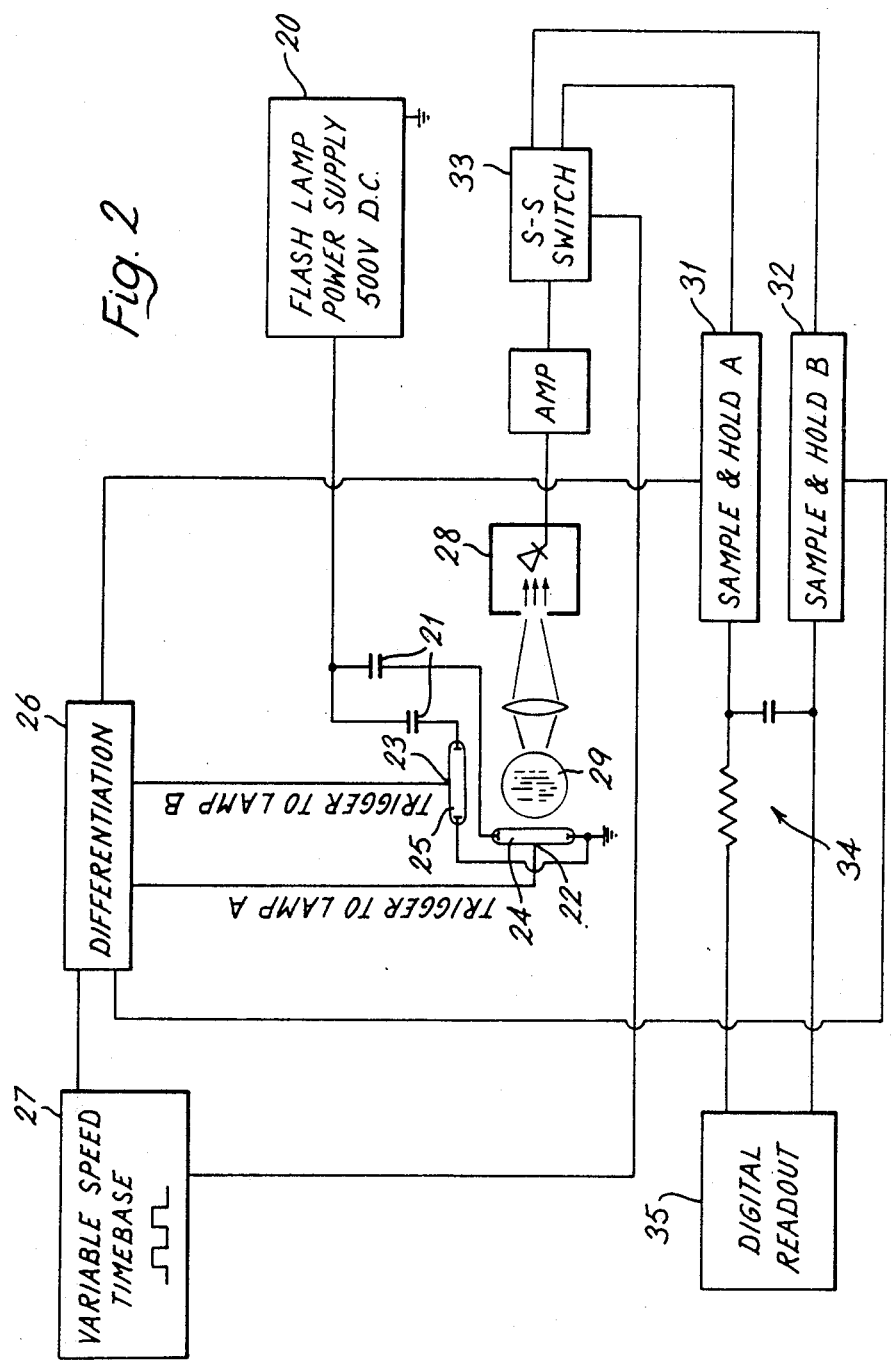

An embodiment of the invention will now be described by way of example, with reference to the accompanying drawings in which:

FIGS. 1a and 1b show in elevation and plan a diagrammatic representation of a portable airborne fibre monitor, and FIG. 2 is a schematic diagram of the electrical layout of the monitor of FIG. 1.

Referring now to the drawings, a pump draws air containing fibres into a slotted inlet nozzle 1 of the instrument where they are aligned by inertia. These aligned fibres are then charged by a corona discharge existing between a wire 2 and a first plate electrode 3. The charged fibres are then precipitated on to a microscope cover slip 4 beneath a conducting glass window 5 connected to a second plate electrode 6 which serves to precipitate the fibres. The electrical potentials on the corona and precipitating electrodes can be varied for each fibre type but are typically 3,000 and 300 volts. Fibers are precipitated on to the cover slip retaining their axial alignment.

The number of fibres is directly related to the light scattering along and across the cover slip, and may be determined accurately by using high stability flash lamps 7, collimated by wedged light pipes 8, along and at right angles to the flow. The difference between alternate pulses is recorded using a single detector 9. This is achieved by switching the output of the detector to two separate, 'sample and hold' chips 31,32 (FIG. 2) and triggering on the maximum of each pulse separately.

The electrical circuit arrangement comprises a 500 volt power supply 20 which charges capacitors 21 coupled to flash-tube discharge electrodes 22,23. The flash tubes 24,25 are positioned along and at right angles to the fibre axes and are illuminated alternately by means of trigger pulses derived from a differentiating circuit 26 fed from a variable speed timebase 27. A photodetector 28 gives an output voltage dependent on the intensity of radiation scattered from fibrous particles on a cover slip 29. This output voltage is amplified by an amplifier 30 and fed to one of a pair of sample-and-hold circuits 31,32 which are synchronized with the timebase by a solid-state switch 33. The output from the sample-and-hold circuits is fed to a comparator 34 and a digital readout device 35 which gives a readout calibrated in terms of the fibre concentration.

By measuring the difference in output between the two chips, a measure of the aligned fibres is made. This output is displayed digitally as voltage, or differentiated giving a rate of change. Thus, the output can be calibrated to give accumulated fibres or an instantaneous measure of concentration. Calibration can be carried out against microscope counts made manually on the cover slip.

The instrument is able to replace the cumbersome microscope method of airborne fibre counting, and in addition allows the instantaneous measure of contamination, which is not possible at present, for much the same capital outlay as for a microscope.

We claim:

1. Apparatus for measuring a quantity of fibres present in a gaseous fluid comprising:
   means for creating a flow of said gaseous fluid through a chamber,
   aligning means for aligning an orientation of fibrous particles flowing into said chamber,
   electrical charging means for charging said particles within said chamber,
   carrier means for providing a surface for said fibrous particles to precipitate thereon,
   electrical precipitating means for precipitating said fibrous particles onto said carrier means,
   illuminating means for illuminating said carrier means with radiation, and
   measuring means for measuring radiation transmitted from said carrier means, thereby to derive an indication of the number of said particles precipitated thereon.

2. Apparatus for measuring the quantity of fibres present in a gaseous fluid as claimed in claim 1 wherein the aligning means comprises a slotted inlet nozzle of the instrument where they are aligned by inertia.

3. Apparatus for measuring the quantity of fibres present in a gaseous fluid as claimed in claim 2 wherein the charging means comprises a wire and a pair of plate electrodes.

4. Apparatus for measuring the quantity of fibres present in a gaseous fluid as claimed in claim 2 incorporating means for applying a voltage of between 300 and 3,000 volts between said wire and said plate electrodes.

5. Apparatus for measuring the quantity of fibres present in a gaseous fluid as claimed in claim 1 wherein said measuring means comprises optical means for measuring the scattering of light by said aligned fibres.

6. Apparatus for measuring the quantity of fibres present in a gaseous fluid as claimed in claim 5 wherein said optical means comprises a pair of light sources adapted to produced collimated radiation in a direction substantially along and normal to the direction of alignment of the particles.

7. Apparatus for measuring the quantity of fibres present in a gaseous fluid as claimed in claim 5 wherein the difference between alternate pulses is recorded using a single detector.

8. Apparatus for measuring the quantity of fibres present in a gaseous fluid as claimed in claim 7 including means adapted to switch the output of a detector to two separate, 'sample and hold' circuits.

9. Apparatus for measuring the quantity of fibres present in a gaseous fluid as claimed in claim 8 further including means to measure the difference in output between said two circuits.

* * * * *